United States Patent [19]

Thyen

[11] 4,135,623
[45] Jan. 23, 1979

[54] PACKAGE FOR ARMED SUTURES
[75] Inventor: Eberhard H. Thyen, Middlesex, N.J.
[73] Assignee: Ethicon, Inc., Somerville, N.J.
[21] Appl. No.: 871,047
[22] Filed: Jan. 20, 1978
[51] Int. Cl.² .............................................. A61L 17/02
[52] U.S. Cl. ................................. 206/63.3; 206/227; 206/380
[58] Field of Search ..................... 206/63.3, 380, 382, 206/381, 227

[56] References Cited

U.S. PATENT DOCUMENTS

| | | | |
|---|---|---|---|
| 3,857,484 | 12/1974 | Thyen ................................. | 206/227 |
| 3,985,227 | 10/1976 | Thyen et al. ........................ | 206/63.3 |
| 4,014,434 | 3/1977 | Thyen ................................. | 206/63.3 |
| 4,034,850 | 7/1977 | Mandel et al. ...................... | 206/63.3 |

Primary Examiner—William T. Dixson, Jr.
Attorney, Agent, or Firm—Wayne R. Eberhardt

[57] ABSTRACT

A one-piece folded package for a plurality of single- or double-armed sutures comprising two suture mounting panels and one intermediate connecting panel. When folded, the panels completely enclose a major portion of the suture strand while the needles are displayed in an area protected by a separate cover flap extending from one panel. The sutures are individually mounted on the two suture mounting panels with the armed end of each suture retained in slits in a foam strip. When the package is opened, the suture mounting panels may be folded to elevate the needles of the sutures in two tiers for easy grasping and removal from the package.

14 Claims, 4 Drawing Figures

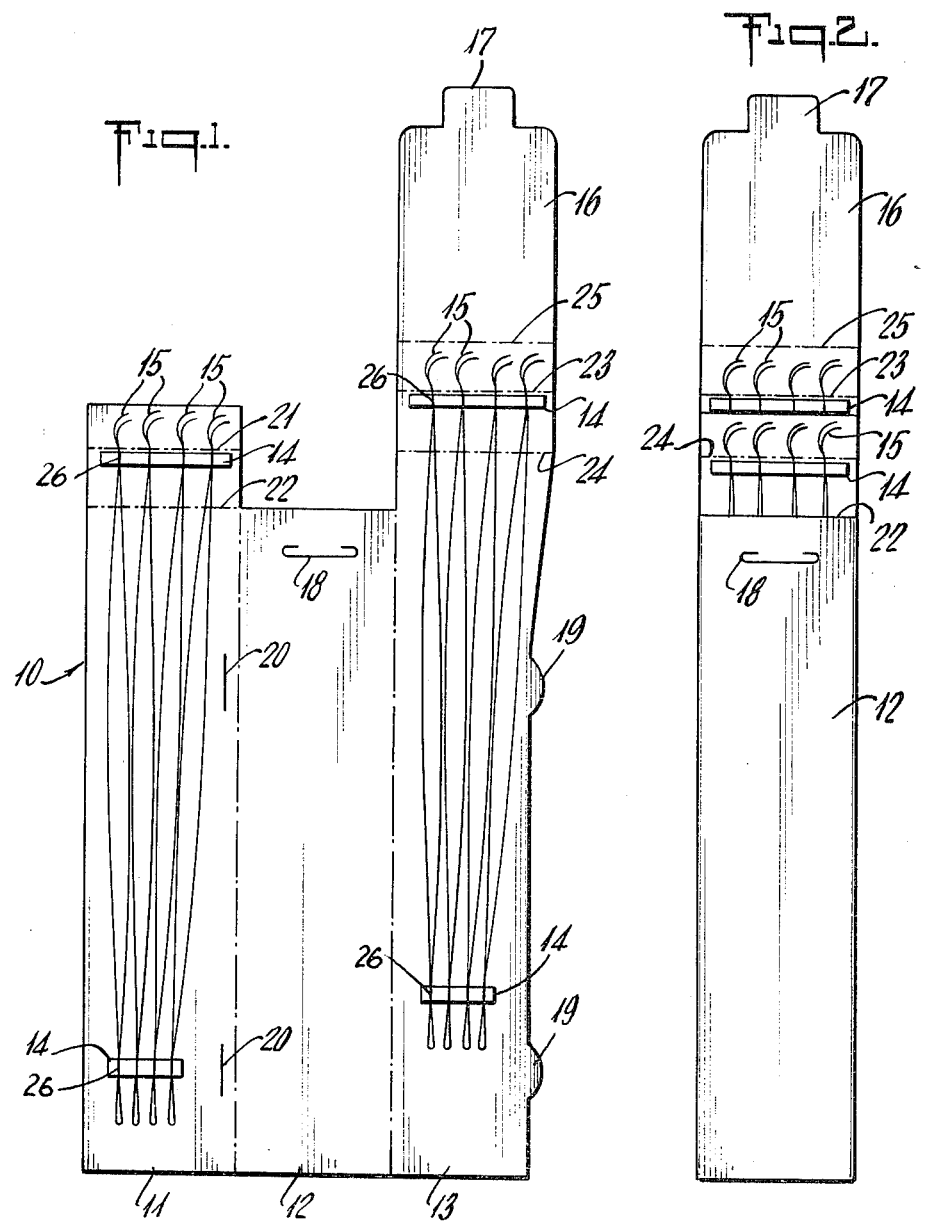

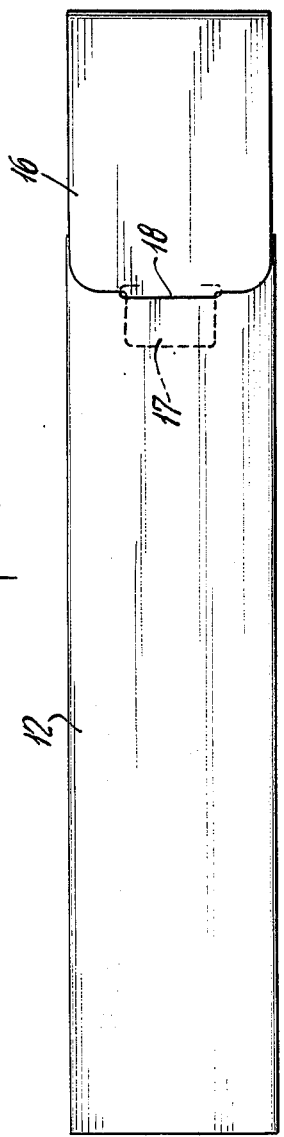
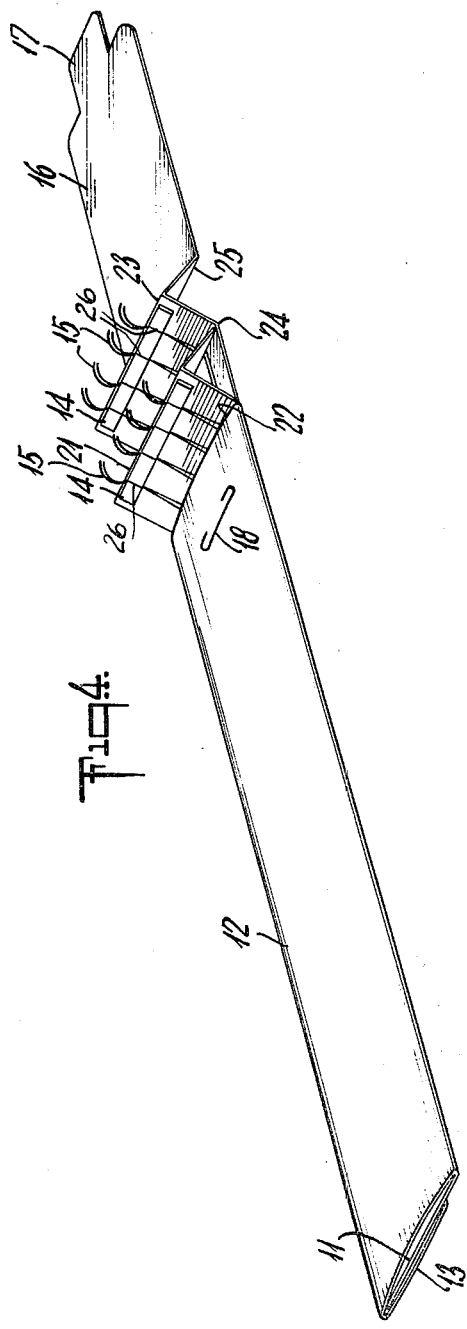

PACKAGE FOR ARMED SUTURES

BACKGROUND OF THE INVENTION

1. Field of the Invention

This invention relates to packages for surgical sutures, and more particularly to folded paperboard packages for holding and dispensing a plurality of individually mounted single- or double-armed sutures.

2. Description of Prior Art

Packages for surgical sutures are constructed according to the nature of the suture and its intended use. In general, suture packages are provided to make the suture readily available to the surgeon with a minimum of handling. This requires that the suture be packaged in a manner that allows the package to be opened and the suture easily removed without entangling the suture with itself or adjacent sutures. It is also desirable that once removed, the suture has a minimum of bends, kinks or tendency to coil. In packaging armed sutures, it is desirable that the needles be readily accessible, and in the case of double-armed sutures, that the needles of individual sutures be maintained as pairs so that the sutures may be removed from the package by grasping either or both of the needles.

As used herein, the term "suture" means elongated, thread-like strands suitable for suturing, ligating, or other surgical procedures, with or without needles attached. The term "single-armed suture" means a suture having a needle affixed to one end, while the term "double-armed suture" means a suture having needles affixed to both ends. The term "suture strand" refers specifically to the elongated, thread-like portion of the suture.

Heretofore, armed sutures have been packaged in various ways intended to minimize formation of kinks, bends and coils. For example, double-armed sutures have been wound in the form of a figure-eight and packaged according to U.S. Pat. No. 3,759,376. The package of this reference is particularly well suited for use with heavy or stiff suture materials, particularly those which tend to set in the configuration of the suture in the package.

U.S. Pat. No. 3,985,227 describes a package specifically designed for fine, cardiovascular sutures having relatively small needles mounted in removable, polymeric blocks. The package of the present invention is also particularly well suited for double-armed cardiovascular sutures which are characterized by a light, flexible suture material and small, curved needles.

It is accordingly an object of the present invention to provide a method and package for mounting a plurality of armed sutures. It is a further object of this invention to provide a package for a plurality of double-armed cardiovascular sutures which provides for easy access to and removal of individual sutures. A yet further object of this invention is to provide a package for a plurality of armed sutures comprising a one-piece folded and self-locking construction. These and other objects will be apparent from the ensuing description and claims.

SUMMARY

A folded package for a plurality of single- or double-armed sutures comprising two suture mounting panels and one interconnecting panel. Sutures are individually mounted on the two suture mounting panels by securing the needle or the suture immediately adjacent the needle in a slit in a foam strip secured near the upper end of each mounting panel. One suture mounting panel is extended to provide a cover flap adapted to fold over and enclose the needles when the loaded package is folded to enclose the suture strands. The other suture mounting panel extends a short distance above the intermediate connecting panel. The foam mounting strips on the two suture mounting panels are offset in order to provide an upper and lower tier of sutures.

When the package is opened, the upper portions of each suture mounting panel including the foam strips are exposed while the major length of the suture strand remains enclosed between the panels of the package. The upper portion of each suture mounting panel is scored for bending above and below the foam strips in order that the foam strips may be elevated to present the needles of the opened package in two tiers for ready grasping and removal.

DESCRIPTION OF DRAWINGS

FIG. 1 is a plan view of a loaded package prior to folding.

FIG. 2 is a plan view of the package of FIG. 1 folded with the cover flap open.

FIG. 3 is a plan view of the package of FIG. 2 with the cover flap closed.

FIG. 4 is a view in perspective of the package of FIG. 2 with the suture mounting panels folded to elevate and present the sutures for removal.

DESCRIPTION OF PREFERRED EMBODIMENTS

The suture packages of the present invention comprise a one-piece, three-panel, folded construction which provides two suture mounting panels and one intermediate cover panel. Each suture mounting panel is provided at the upper end with a foam strip across the width of the panel having slits therein for securing the armed ends of the sutures. An optional second foam strip with slits may be provided at the lower end of the mounting panel for securing the suture strand in order to facilitate loading and folding of the package.

The foam strips and the upper ends of the panels are offset on the major axis of the package in order to display two tiers of needled sutures when the package is opened. One suture mounting panel is extended to form a cover flap which may be folded forward to enclose the needle display area, and appropriate interlocking slits and tabs are provided along the edges of the panels to lock the folded package in the folded configuration.

Referring now to FIG. 1, there is illustrated a preferred embodiment of the package of the present invention generally indicated at 10 composed of panels 11, 12 and 13. Panels 11 and 13 are provided at the upper and lower ends thereof with foam strips 14 having a plurality of suture retaining slits 26 therein. Sutures 15 are individually mounted on panels 13 and 14 by securing each suture in a separate slit in the upper and lower foam strips. As illustrated, needles 16 extend above the foam strips in order to facilitate later removal of the sutures from the package as hereinafter explained.

Panel 13 is extended beyond fold line 25 to form cover flap 16 having tab 17 adapted to interlock with slit 18 of panel 12 when the package is folded and closed.

Panel 13 is also provided with tabs 19 adapted to interlock with slits 20 in panel 11 when the three panels of the package are folded to enclose the sutures.

Panel 11 has fold lines 21 and 22 at the upper end thereof which allow the foam strip and needles secured therein to be elevated for easy removal of the sutures as illustrated in FIG. 4. Panel 13 has corresponding fold lines indicated as 23 and 24.

FIG. 2 illustrates the package of FIG. 1 after panels 11 and 12 have been folded over panel 13 and folded package has been locked in place by means of tabs 19 interlocking with slits 20. As illustrated, the sutures mounted on panels 11 and 13 appear as two spaced tiers of needles secured in foam strips 14.

FIG. 3 illustrates the package of FIG. 2 with cover flap 16 of panel 13 folded along line 25 to cover the needle display area and with tab 17 interlocked with slit 18.

FIG. 4 illustrates the package of FIG. 3 opened and ready for suture removal with panels 11 and 13 folded to elevate the foam strips and the needles of the sutures mounted therein. As illustrated, panel 11 is folded forward on line 22 and backward on line 21. Panel 13 is similarly folded forward on line 24 and backward on line 23. The upper edge of panel 11 abuts panel 13 at fold line 24 and is thereby maintained in the desired folded configuration.

As illustrated in FIG. 4, the opened package lies flat with the needled ends of the sutures elevated in two tiers. The elevated needles are easily grasped with a needle holder or by hand in order to withdraw the sutures from between the panels of the package.

The packages of the present invention are preferably constructed of a heavy weight paperboard which can be die cut to the desired shape and scored for folding. Other thin, foldable materials such as sheet plastics or rigid plastic foams may be substituted for paperboard if desired. Foam strips 14 are preferably 5 to 10 mm wide, at least 3 mm thick and slit to a depth of from about 1 to 2 mm. The foam strips are most conveniently cemented in place on the panels. A preferred foam is a high density polyethylene although other materials may also be used with good results. Alternatively, the needles may be mounted by piercing a foam or solid resilient polymeric strip although such needle mounting technique makes the needles less convenient for removal from the package.

Other obvious variations in package construction or design as disclosed herein will be apparent to those skilled in the art. For example, it will be appreciated that single-armed sutures could be packaged with the single needle mounted in the needle display area and the remainder of the suture contained within the package. It may also be desirable to mount sutures on only one panel where there are to be, for example, only four sutures to a package which has a capacity for eight or more sutures. Many other variations of the present invention which nevertheless employ the three panel, one-piece folded construction and double-tier needle display and presentation features of the packages of the present invention will be apparent to those skilled in the art, and such variations are accordingly included within the scope of the present invention.

What is claimed is:

1. A suture package comprising a front panel, an inner panel, and a back panel, said inner panel extending beyond the top of said front panel and said back panel extending beyond the top of said inner panel, said inner panel having suture mounting means affixed across the width of the panel intermediate the top of said inner panel and the top of said front panel, and having first and second fold lines extending across the width of the panel immediately above said needle mounting means and immediately above the top of said front panel, said back panel having suture mounting means affixed across the width of the panel intermediate the top of said back panel and the top of the suture mounting means on said inner panel, and having first and second fold lines extending across the width of said panel immediately above said needle mounting means and a spaced distance below said needle mounting means corresponding to the distance between the first and second fold lines of said inner panel, at least one armed suture mounted on at least one of said inner and back panels with the needled end of said armed suture secured in the suture mounting means and the bulk of said suture strand enclosed between two panels of the package, and a cover flap extending from the top of said back panel and attached thereto by a fold line, said cover flap being foldable over said inner and back panels, whereby, when said cover flap is folded over said inner and back panels the suture mounting means are enclosed thereby, and when said cover flap is open, the suture mounting means on said inner and back panels are exposed and may be elevated by folding said inner and back panels on the fold lines above and below their respective suture mounting means to provide a double tier of needled sutures for removal from the package.

2. A package of claim 1 wherein said inner panel and said back panel are foldably connected to said front panel.

3. A package of claim 2 wherein said panels have integral locking means for maintaining said panels in said folded configuration.

4. A package of claim 3 wherein said integral locking means comprise a tab on the outside edge of said back panel and a corresponding slit on said inner panel adapted to receive and hold said tab of said back panel.

5. A package of claim 1 wherein said suture mounting means comprise a foam strip having suture receiving slits therein.

6. A package of claim 5 wherein said foam strip is at least about 3 mm thick and said slits are from about 1–2 mm deep.

7. A package of claim 5 wherein said foam strip has a width of about 5–10 mm in the direction of the slits.

8. A package of claim 1 wherein said inner and back panels have suture mounting means affixed near the bottom of said panels.

9. A package of claim 8 wherein said suture mounting means comprise a foam strip having suture receiving slits therein.

10. A package of claim 9 wherein said foam strip is at least about 3 mm thick and said slits are from about 1–2 mm deep.

11. A package of claim 1 wherein said cover flap has a tab and said front panel has a corresponding slit adapted to receive and hold said tab when said cover flap is folded over said inner and back panels.

12. A package of claim 1 wherein said package contains more than one armed suture mounted on each of said inner and back panels.

13. A package of claim 1 wherein the armed sutures are double-armed and both needled ends of the suture are secured in said suture mounting means with the needles extending above said mounting means.

14. A package of claim 1 wherein said package is constructed of paperboard.